(12) United States Patent
Prais

(10) Patent No.: US 12,734,306 B2
(45) Date of Patent: Sep. 15, 2026

(54) RIGID NEEDLE SHIELD FOR PREFILLABLE STAKED NEEDLE SYRINGE

(71) Applicant: Becton, Dickinson and Company, Franklin Lakes, NJ (US)

(72) Inventor: Alfred W. Prais, Hewitt, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1108 days.

(21) Appl. No.: 17/676,588

(22) Filed: Feb. 21, 2022

(65) Prior Publication Data

US 2023/0263963 A1 Aug. 24, 2023

(51) Int. Cl.
*A61M 5/32* (2006.01)
*A61M 5/31* (2006.01)

(52) U.S. Cl.
CPC .......... *A61M 5/3202* (2013.01); *A61M 5/321* (2013.01); *A61M 2005/3109* (2013.01); *A61M 2005/3206* (2013.01); *A61M 2005/3246* (2013.01)

(58) Field of Classification Search
CPC .. A61M 5/3202; A61M 5/321; A61M 5/3213; A61M 5/50; A61M 5/5086; A61M 2005/3109; A61M 2005/3206; A61M 2005/3212; A61M 2005/3215; A61M 2005/3217; A61M 2005/3231; A61M 2005/3246; A61M 2005/3254; A61M 2005/3258
See application file for complete search history.

(56) References Cited

U.S. PATENT DOCUMENTS 4,474,734 A 10/1984 Cooper
5,098,400 A * 3/1992 Crouse ................ A61M 5/3204 604/263
5,858,008 A 1/1999 Capaccio
7,641,636 B2 * 1/2010 Moesli ................ A61M 5/3202 604/164.08
9,084,854 B2 7/2015 Evans et al.
2003/0181859 A1 * 9/2003 Brunel ................ A61M 5/3202 604/192
2004/0030303 A1 2/2004 Prais et al.
2016/0106929 A1 * 4/2016 Fournier ............ A61M 5/3202 604/192
2016/0243315 A1 * 8/2016 Perche ................ A61M 5/3204
2018/0344944 A1 12/2018 Wendland et al.
2021/0402102 A1 * 12/2021 Timmis ............... A61M 5/3204

FOREIGN PATENT DOCUMENTS

AU 2012279539 2/2014
WO 2022248474 A1 12/2021

* cited by examiner

*Primary Examiner* — Wesley G Harris
*Assistant Examiner* — Charles W Nichols
(74) *Attorney, Agent, or Firm* — The Webb Law Firm

(57) ABSTRACT

A rigid needle shield for a syringe includes a main body comprising an internal sidewall defining a bore, and an end cap attached to the main body. The end cap includes at least one frangible tab connected to the sidewall of the main body. The rigid needle shield further includes an elastomeric insert extending through the bore and engaging the end cap. The at least one frangible tab is configured to break from the internal sidewall and advance through the bore upon application of a force to the end cap.

17 Claims, 8 Drawing Sheets

RIGID NEEDLE SHIELD FOR PREFILLABLE STAKED NEEDLE SYRINGE

BACKGROUND OF THE INVENTION

Field of the Invention

The present disclosure relates to medical syringes and to needle shields for medical syringes.

Description of Related Art

Syringes are used in a wide variety of medical procedures in order to deliver various substances to patients, to create fluid connections, and to transfer liquids between containers. To protect users from accidentals needle sticks, prevent leakage of the syringe contents out of the needle tip, and prevent contamination entering the needle tip, syringes may be equipped with a rigid needle shield (RNS). One conventional RNS design includes a rubber insert that the needle tip pierces and embeds in as the RNS is attached to the syringe. The rubber insert has the effect of plugging the needle tip to prevent leakage from the syringe and contamination from entering through the needle tip.

Conventional rubber inserts, however, have several drawbacks. Insertion of the needle into the rubber insert generates friction that can rub pre-applied lubricant off of the needle. Further, the rubber insert used in the RNS generally includes filler material, such as clay or minerals, to improve strength and durability. However, these filler materials are abrasive and therefore dull the needle tip as the needle is inserted into the rubber insert. Both of these effects—the removal of lubricant and dulling of the needle tip—make subsequent insertion of the needle into the patient more difficult and painful. Additionally, the needle tends to deflect during insertion into the rubber insert due to the beveled face of the needle tip. This can result in bending or breakage of the needle, particularly for smaller needles (e.g. 25 gauge and smaller) and needles with thin sidewalls.

SUMMARY

Embodiments of the present disclosure are directed to a needle shield for a syringe. The needle shield includes a main body including an internal sidewall defining a bore, and an end cap attached to the main body. The end cap includes at least one frangible tab connected to the sidewall of the main body. The rigid needle shield further includes an elastomeric insert extending through the bore and engaging the end cap. The at least one frangible tab is configured to break from the internal sidewall and advance through the bore upon application of a force to the end cap.

In some embodiments, each of the at least one frangible tabs includes a ramped surface configured to cause the frangible tab to deflect radially inward to allow the frangible tab to advance through the bore.

In some embodiments, each of the at least one frangible tabs includes a locking surface configure to engage a shoulder of the main body.

In some embodiments, engagement of the locking surface and the shoulder prohibits proximal movement of the end cap relative to the main body.

In some embodiments, the elastomeric insert defines an internal cavity having a needle bore for receiving a needle of the syringe.

In some embodiments, the needle bore is sized for a clearance fit with the needle of the syringe.

In some embodiments, deflection of the at least one frangible tab causes compression of the elastomeric insert and reduces the diameter of the needle bore.

In some embodiments, the elastomeric insert includes a distal lip configured to engage a lip surface of the end cap.

In some embodiments, the at least one frangible tab is arranged in a ring about the bore.

In some embodiments, the end cap defines a gap between adjacent frangible tabs.

In some embodiments, the rigid needle shield comprises two, three, or four frangible tabs integrally formed with the main body.

In some embodiments, a body of the elastomeric insert is tapered.

Other embodiments of the present disclosure are directed to a system including a syringe including a barrel and a needle, and a rigid needle shield attached to a distal end of the syringe. The rigid needle shield includes a main body including an internal sidewall defining a bore, and an end cap attached to the main body. The end cap includes at least one frangible tab connected to the sidewall of the main body, and an elastomeric insert extending through the bore and engaging the end cap. The at least one frangible tab is configured to break from the internal sidewall and advance through the bore upon application of a force to the end cap.

In some embodiments, a proximal end of the rigid needle shield engages the barrel of the syringe.

In some embodiments, the at least one frangible tab is configured to break after the proximal end of the rigid needle shield has engaged the barrel of the syringe.

In some embodiments, the elastomeric insert defines a needle bore having a clearance fit with the needle.

In some embodiments, deflection of the at least one frangible tab causes compression of the elastomeric insert and squeezes the needle to seal a tip of the needle.

In some embodiments, a tip of the needle does not pierce the elastomeric insert in order to enter the needle bore.

In some embodiments, the elastomeric insert defines a proximal bore configured to engage a tip of the barrel of the syringe.

In some embodiments, the needle is 25 gauge or smaller.

Further details and advantages of the various examples described in detail herein will become clear upon reviewing the following detailed description of the various examples in conjunction with the accompanying drawing figures.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
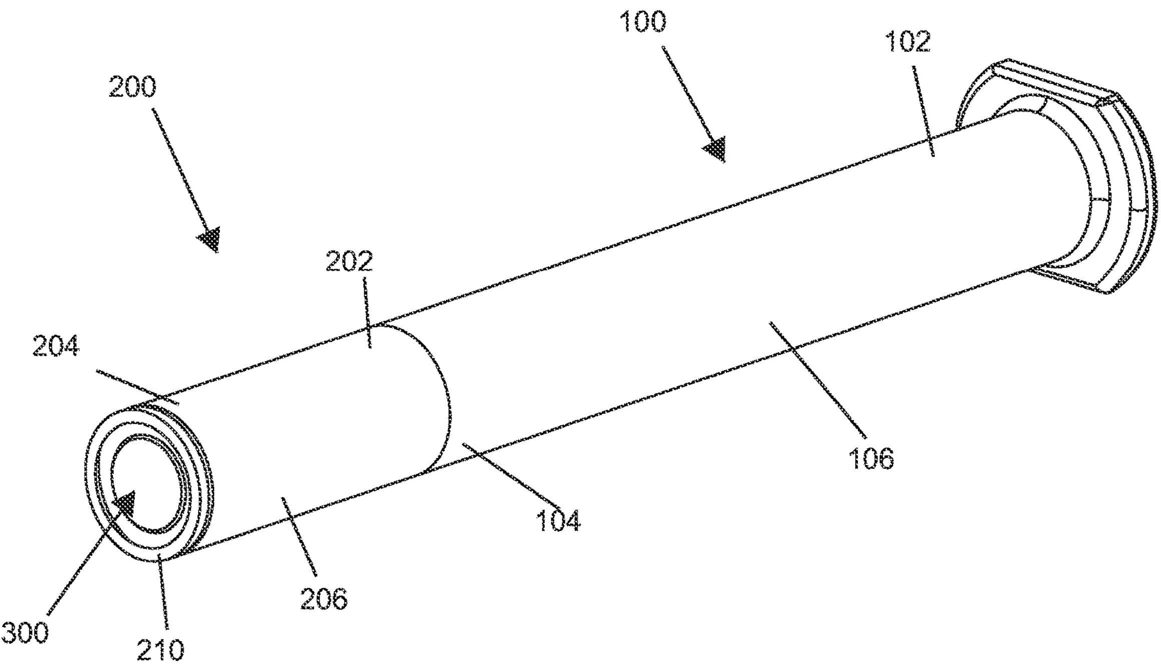
FIG. 1 is a perspective view of a syringe equipped with a rigid needle shield (RNS) according to an embodiment of the present disclosure.

The following description is provided to enable those skilled in the art to make and use the described aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

All numbers used in the specification and claims are to be understood as being modified in all instances by the term "about". The terms "approximately", "about", and "substantially" mean a range of plus or minus ten percent of the stated value. Further, the term "substantially equal" and like terms mean that the compared values or dimensions are within a range of plus or minus ten percent of one another.

The terms "first", "second", and the like are not intended to refer to any particular order or chronology, but refer to different conditions, properties, or elements.

As used herein with reference to an injection apparatus such as a syringe, the term "proximal" refers to an end of the apparatus farthest from the outlet, or to a direction toward the end of the apparatus farthest from the outlet. As used herein with reference to an injection apparatus such as a syringe, the term "distal" refers to an end of the device or apparatus closest to the outlet, or to a direction toward the end of the apparatus closest to the outlet.

As used herein, "at least one of" is synonymous with "one or more of". For example, the phrase "at least one of A, B, and C" means any one of A, B, or C, or any combination of any two or more of A, B, or C. For example, "at least one of A, B, and C" includes one or more of A alone; or one or more of B alone; or one or more of C alone; or one or more of A and one or more of B; or one or more of A and one or more of C; or one or more of B and one or more of C; or one or more of all of A, B, and C.

Figure 2:
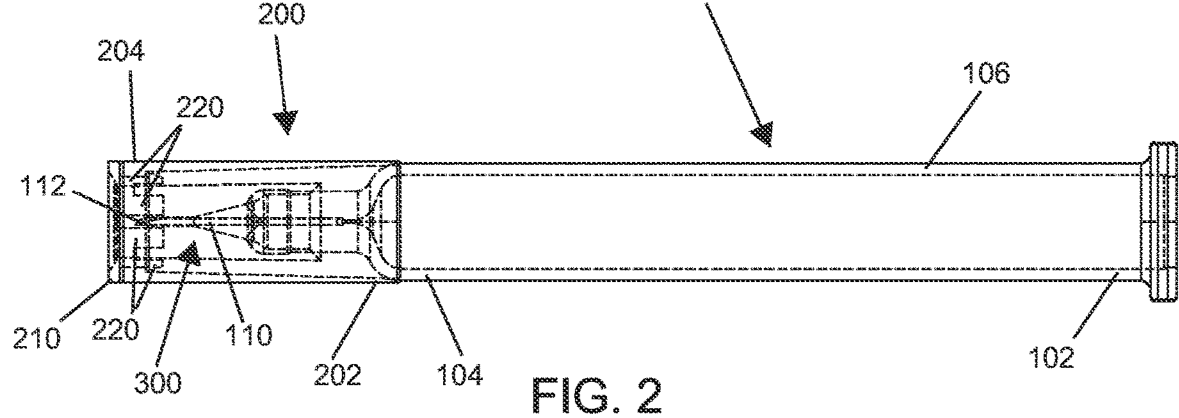
FIG. 2 is a side view of the syringe and RNS of FIG. 1.

Referring first to FIGS. 1 and 2, a syringe 100 having proximal end 102 and a distal end 104 is illustrated. The syringe 100 includes a needle 110 which may be adhesively bonded to a barrel 106 of the syringe 100 in a staked needle configuration. A rigid needle shield (hereinafter "RNS") 200 is attached to the distal end 104 of the syringe 100 to shield the needle 110 of the syringe 100 and to prevent leakage of fluid contained within a barrel 106 of the syringe 100. The RNS 200 includes a main body 206, a proximal end 202 that interfaces with the barrel 106 of the syringe 100, and a distal end 204 extending distally beyond the needle 110. The RNS 200 houses an elastomeric insert 300 that engages a tip 112 of the needle 110 when the RNS 200 is fully seated on the syringe 100. The elastomeric insert 300 seals the tip 112 of the needle 110 to prevent leakage of the contents of the barrel 106 of the syringe 100. The distal end 204 of the RNS 200 includes an end cap 210 that retains the elastomeric insert 300 in the RNS 200. As will be described in detail herein in connection with FIGS. 5-16, the end cap 210 includes one or more frangible tabs 220 that are connected to the main body 206 of the RNS 200. The frangible tabs 220 are configured to break from the main body 206 as the RNS 200 is attached to the syringe 100, allowing the end cap 210 and the elastomeric insert to move proximally with respect to the main body 206. In FIGS. 1 and 2, the RNS 200 is shown fully installed on the syringe 100, such that the frangible tabs 220 have been broken and the end cap 210 and the elastomeric insert 300 have moved proximally with respect to the main body 206. The number of frangible tabs 220 may be two or greater, for example three or four. However, there is not an upper limit to the number of frangible tabs 220, though too many may introduce manufacturing challenges or produce tabs which are prone to failing.

Figure 3:
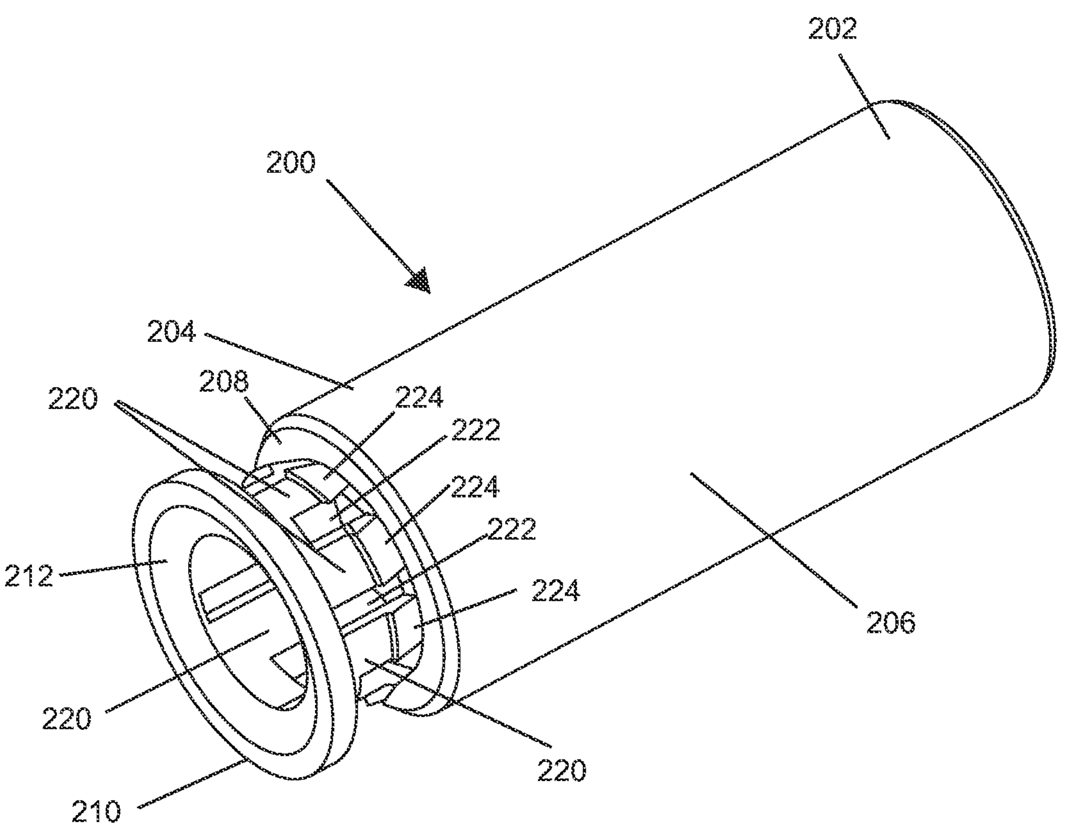
FIG. 3 is a perspective view of the of the RNS of FIG. 1, prior to attachment to the syringe, with an elastomeric insert removed for clarity.
Figure 4:
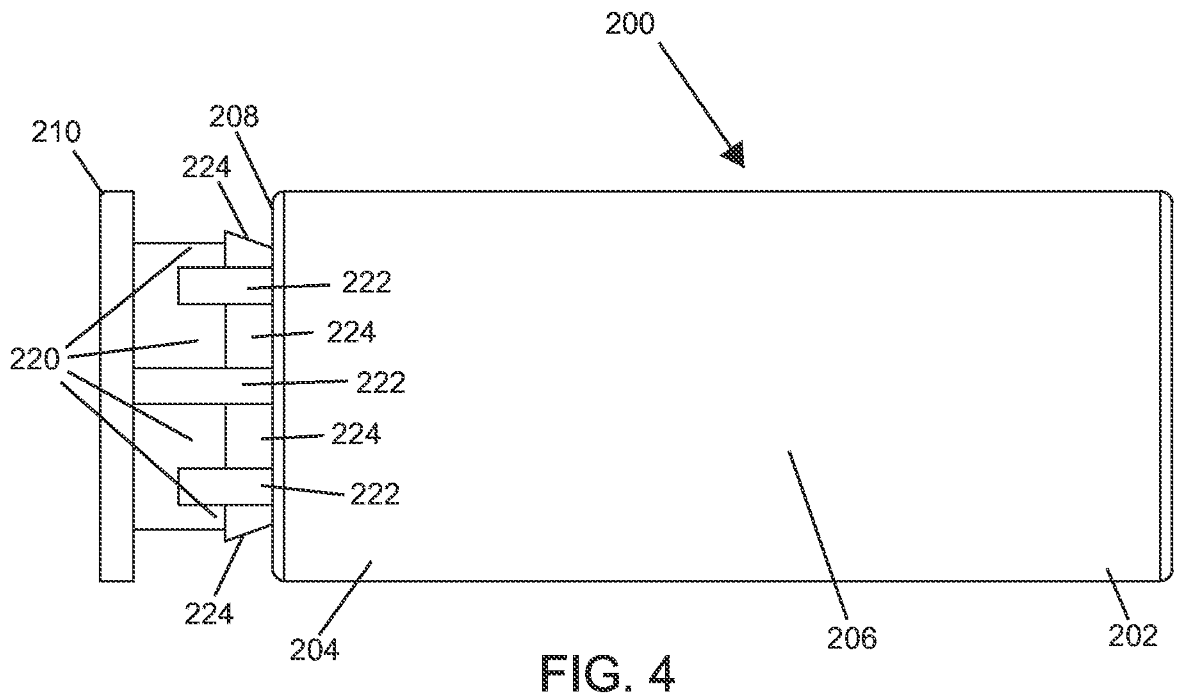
FIG. 4 is a side view of the RNS of FIG. 3.
Figure 5:
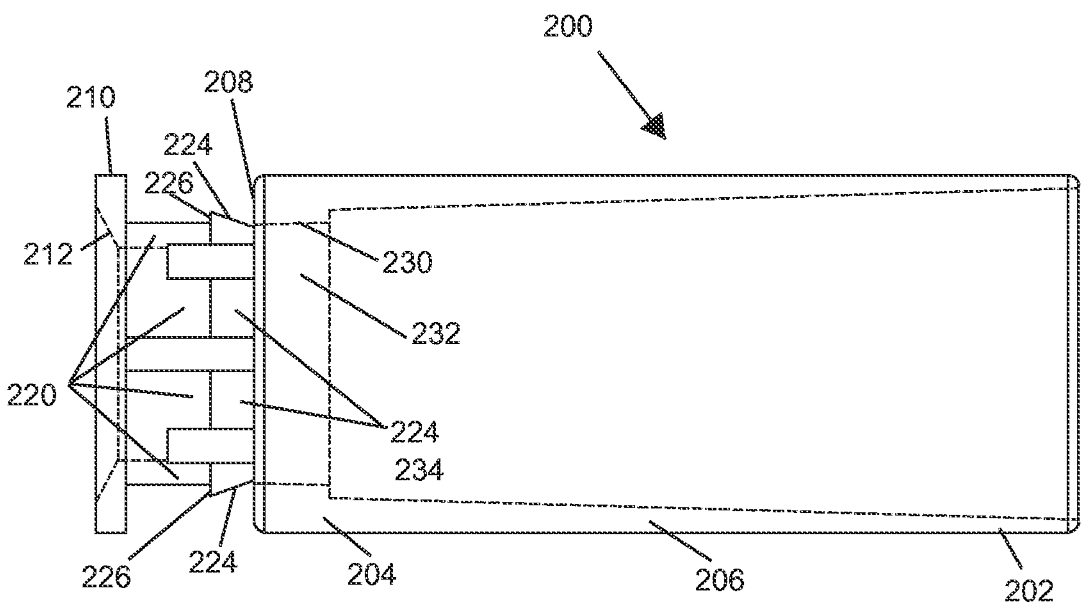
FIG. 5 is a side view of the RNS of FIG. 3.

Referring now to FIGS. 3-5, the RNS 200 is illustrated prior to attachment to the syringe 100, with the elastomeric insert 300 removed so that other features of the RNS 200 may be better appreciated. As noted above, the frangible tabs 220 are connected to the main body 206, and in particular the frangible tabs 220 are connected to an internal sidewall 230 defining a bore 232. In some embodiments the frangible tabs 220 may be integrally formed with the main body 206, for example during an injection molding process. The connection between the frangible tabs 220 and the sidewall 230 is weak enough that the connection can be broken by a proximally-directed force applied to the end cap 210. In particular, the connection between the frangible tabs 220 and the internal sidewall 230 is designed so that a human or robot attaching the RNS 200 to the syringe 100 is able to break the connection without otherwise damaging the syringe 100 or the RNS 200. The amount of force required to break the connection between the frangible tabs 220 and the internal sidewall 230 is a function of several variables, including but not limited to: the material of the RNS; the number of frangible tabs 220; and the cross-sectional area of the material connecting the frangible tabs 220 to the internal sidewall 230.

The frangible tabs 220 are arranged in a ring about the bore 232, with a gap 222 between adjacent frangible tabs 220. Each of the frangible tabs 220 includes a ramped surface 224 that tapers radially outward in a distal direction. The distal end of the ramped surface 224 defines a locking surface 226 extending substantially perpendicular to the longitudinal axis of the RNS 200. With the frangible tabs 220 still attached to the sidewall 230, the outer circumference of the locking surface 226 is greater than the internal diameter of the bore 232. However, once the frangible tabs 220 have been broken from the sidewall 230 by a force applied to the end cap 210, the ramped surfaces 224 cause the frangible tabs 220 to deflect radially inward to allow the frangible tabs 220 to pass through the bore 232. Deflection of the frangible tabs 220 is also facilitated by the gaps 222 between the frangible tabs 220, which provide relief to allow the frangible tabs 220 to move relative to on another. The force required to cause the frangible tabs 220 to pass through the bore 232 is a function of the slope of the ramped surfaces 224 the length of the frangible tabs 220, and the spacing between the frangible tabs 220 (i.e. the width of the gaps 222). Continued application of a force to the end cap 210 causes the frangible tabs 220 to advance through the bore 232 until the locking surfaces 226 clear the proximal end of the bore 232, at which point the frangible tabs 220 are free to deflect radially outward. The locking surface 226 of the frangible tabs 220 then engages a shoulder 234 of the main body 206 to lock the end cap 210 in place. Further illustration of the action of the frangible tabs 220 is provided in FIGS. 13-16, which will be described later.

Figure 6:
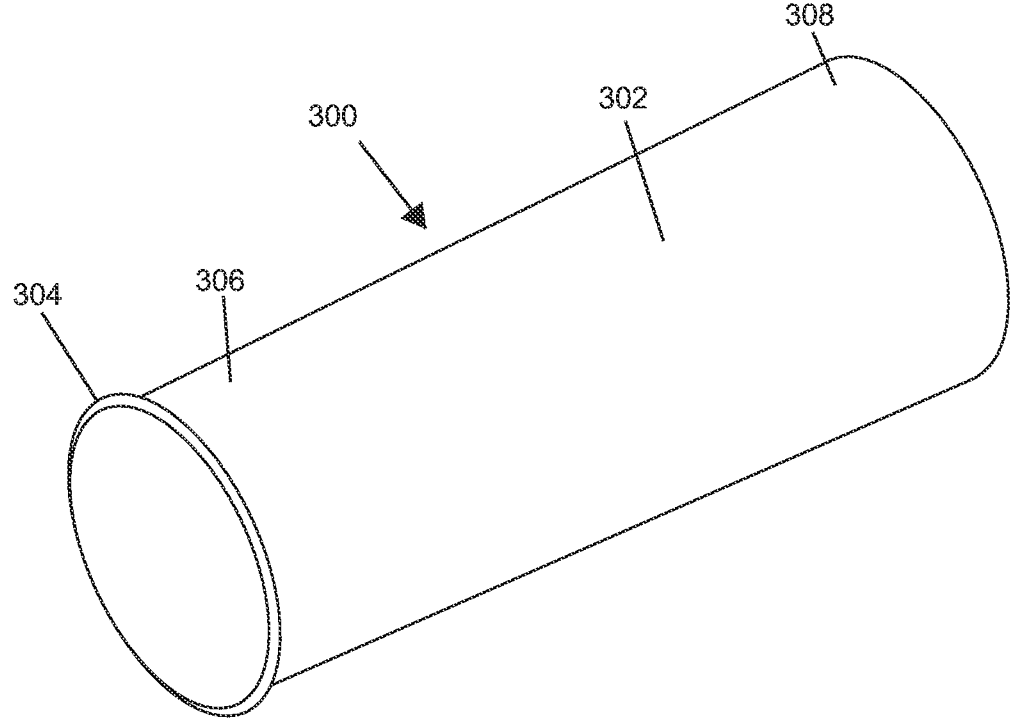
FIG. 6 is a perspective view of an elastomeric insert for the RNS of FIG. 3.
Figure 7:
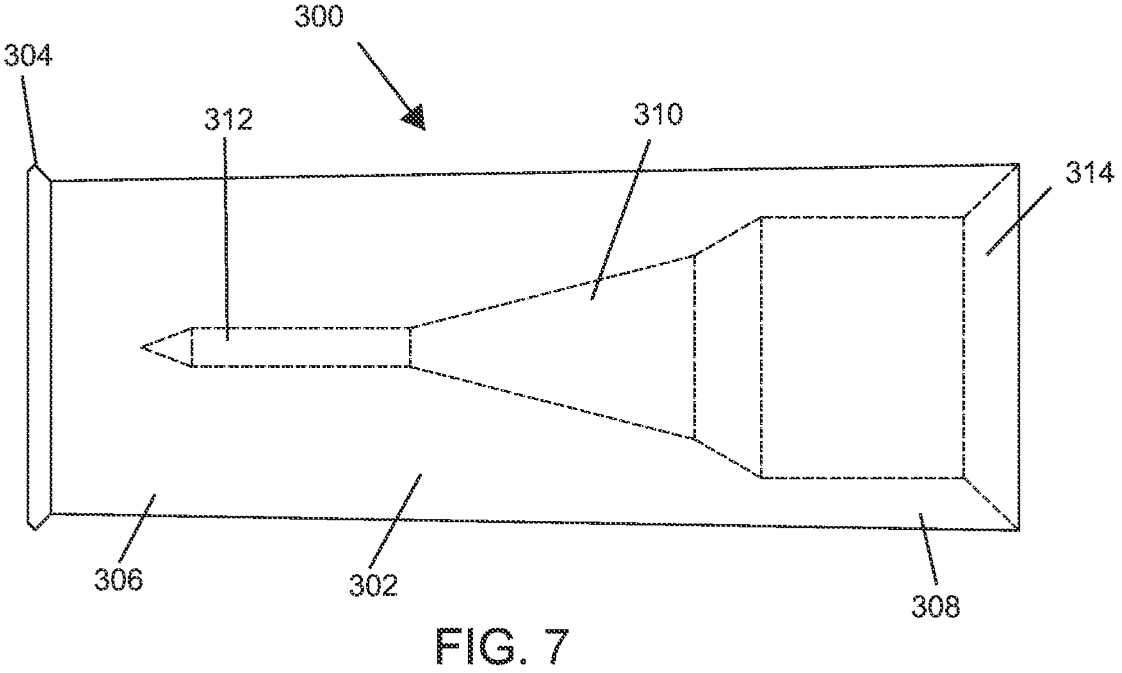
FIG. 7 is a side view of the elastomeric insert of FIG. 6.

With continued reference to FIGS. 3-5 and further reference to FIGS. 6-7, the main body 206 of the RNS 200 is hollow to receive the elastomeric insert 300 (as shown in FIG. 2). The elastomeric insert 300 is made from a resilient material, such as rubber, thermoplastic elastomer (TPE), thermoplastic polyolefin (TPO), thermoplastic vulcanizate (TPV) or the like, that allows the elastomeric insert 300 to reversibly deform during assembly of the elastomeric insert 300 to the RNS 200 and during attachment of the RNS 200 to the syringe 100. The end cap 210 of the RNS 200 defines a lip surface 212 to receive a distal lip 304 (see FIG. 6) of the elastomeric insert 300. As shown in FIGS. 6 and 7, the distal lip 304 extends radially outward from a distal end 306 of a body 302 of the elastomeric insert 300, and the distal lip 304 is configured to engage the lip surface 212 of the end cap 210 when the elastomeric insert 300 is assembled with the RNS 200. The body 302 of the elastomeric insert 300 may be tapered or frusto-conical to position the elastomeric insert 300 in the RNS 200.

Referring in particular to FIG. 7, the elastomeric insert 300 defines an internal cavity 310 configured for sealing the needle 110 of the syringe 100. The distal end 306 of the body 302 is closed, while a proximal end 308 of the body 302 is open to receive the needle 110 as the RNS 200 is attached to the syringe 100. The internal cavity 310 of the body 302 includes a needle bore 312 configured to receive the needle 110. The internal diameter of the needle bore 312 can be a clearance fit relative to the needle 110, such that the needle bore 312 does not substantially abrade the needle 110 as the RNS 200 is slid onto the syringe 100. Thus, the needle bore 312 does not rub off any lubricant pre-applied to the needle 110. In some embodiments, lubricant may alternatively or additionally be applied to the body 302 of the elastomeric insert 300. Proximally of the needle bore 312, the internal cavity 310 of the body 302 increases in diameter, for example by one or more tapers or steps. A proximal bore 314 of the internal cavity 310 may be configured to engage a tip of the barrel 106 of the syringe 110 (as shown in FIG. 2). In some embodiments, the interface between the internal cavity 310 and the barrel 106 serves as a sterile barrier to prevent contamination of the needle 110.

Figure 8:
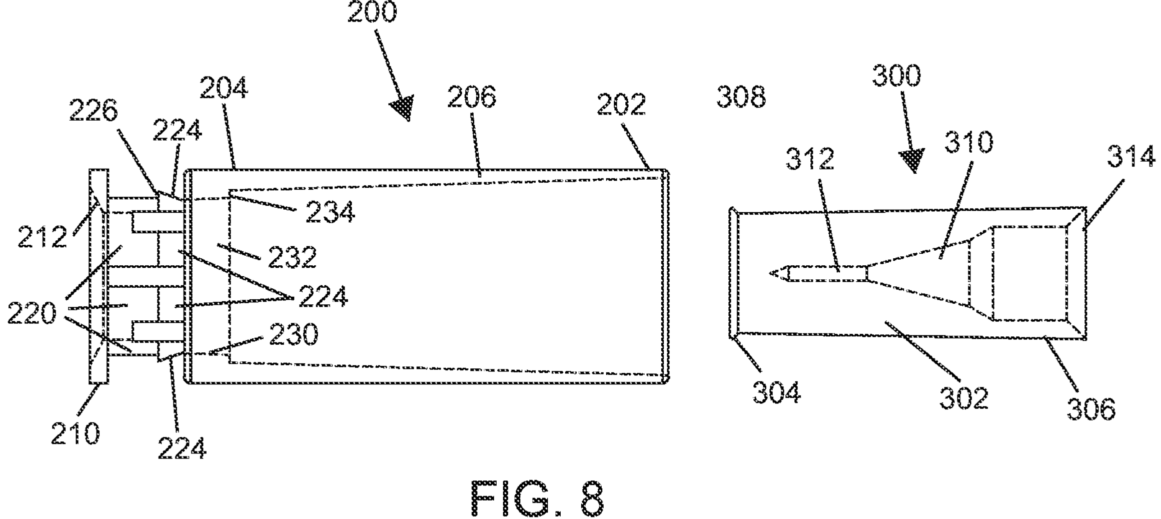
FIG. 8 is an exploded side view of the RNS of FIG. 3.
Figure 9:
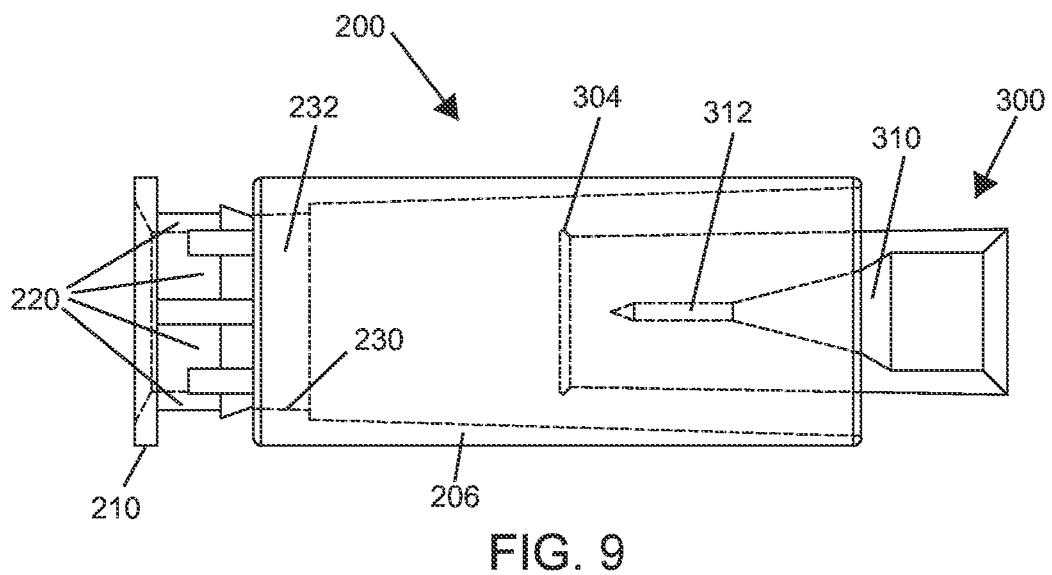
FIG. 9 is a side view of the elastomeric insert of FIG. 6, partially inserted into the RNS of FIG. 3.
Figure 10:
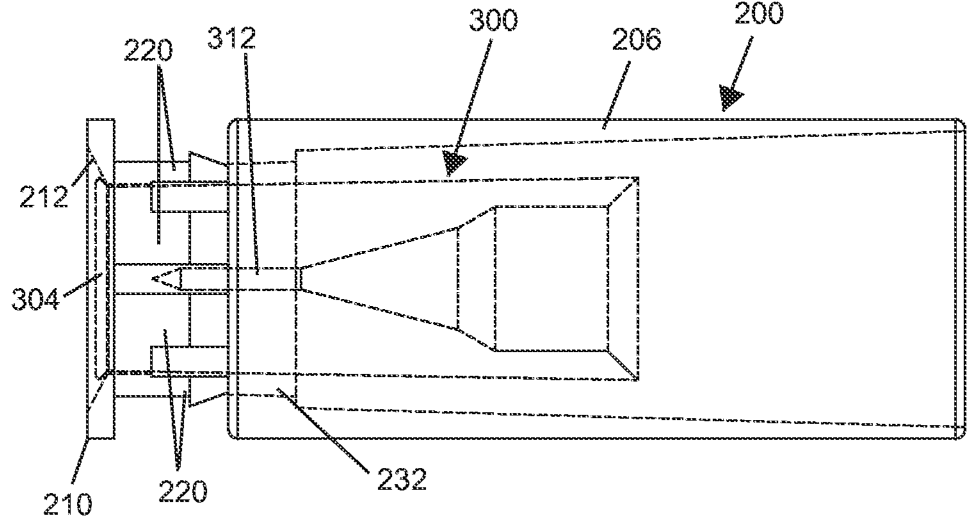
FIG. 10 is a side view of the RNS of FIG. 3.
Figure 11:
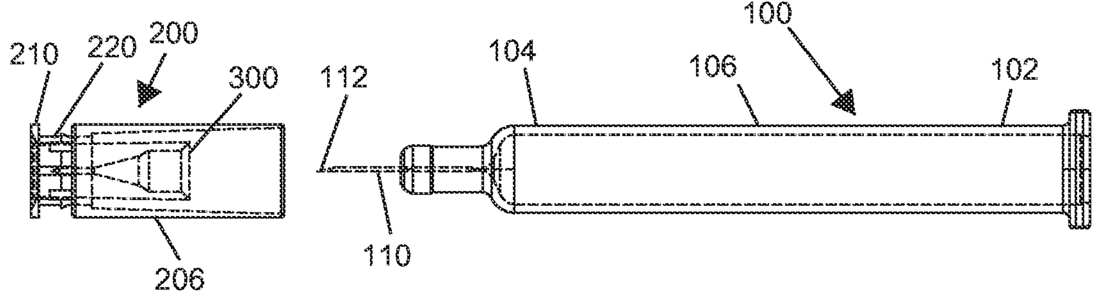
FIG. 11 is an exploded side view of the syringe and the RNS of FIG. 1.
Figure 12:
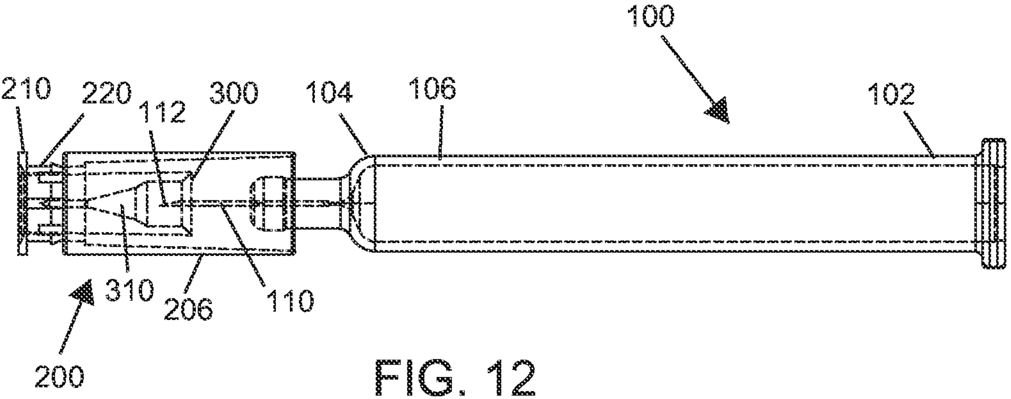
FIG. 12 is a side view of the RNS partially installed on the syringe of FIG. 1.
Figure 13:
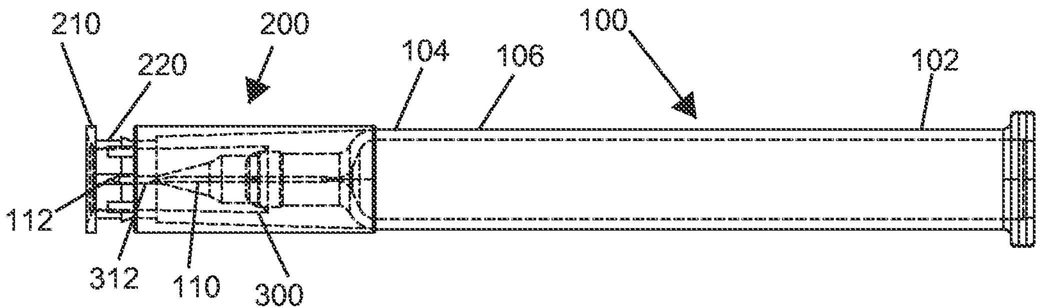
FIG. 13 is a side view of the RNS partially installed on the syringe of FIG. 1.
Figure 14:
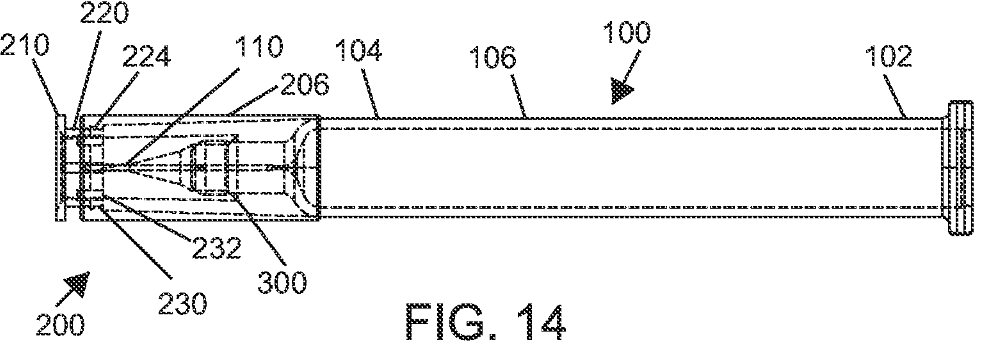
FIG. 14 is a side view of the RNS partially installed on the syringe of FIG. 1.
Figure 15:
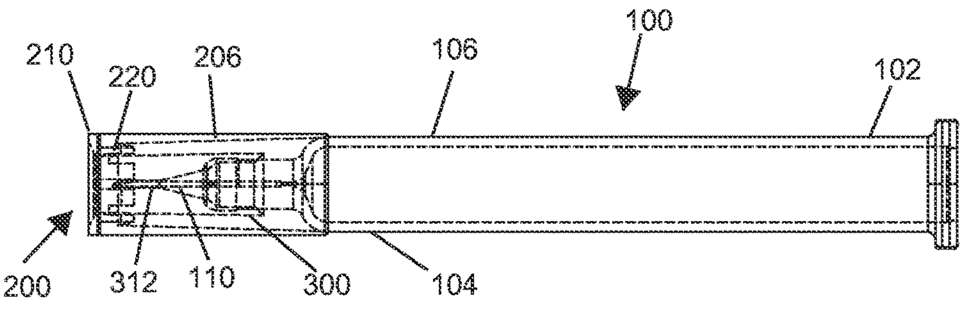
FIG. 15 is a side view of the RNS fully installed on the syringe of FIG. 1.
Figure 16:
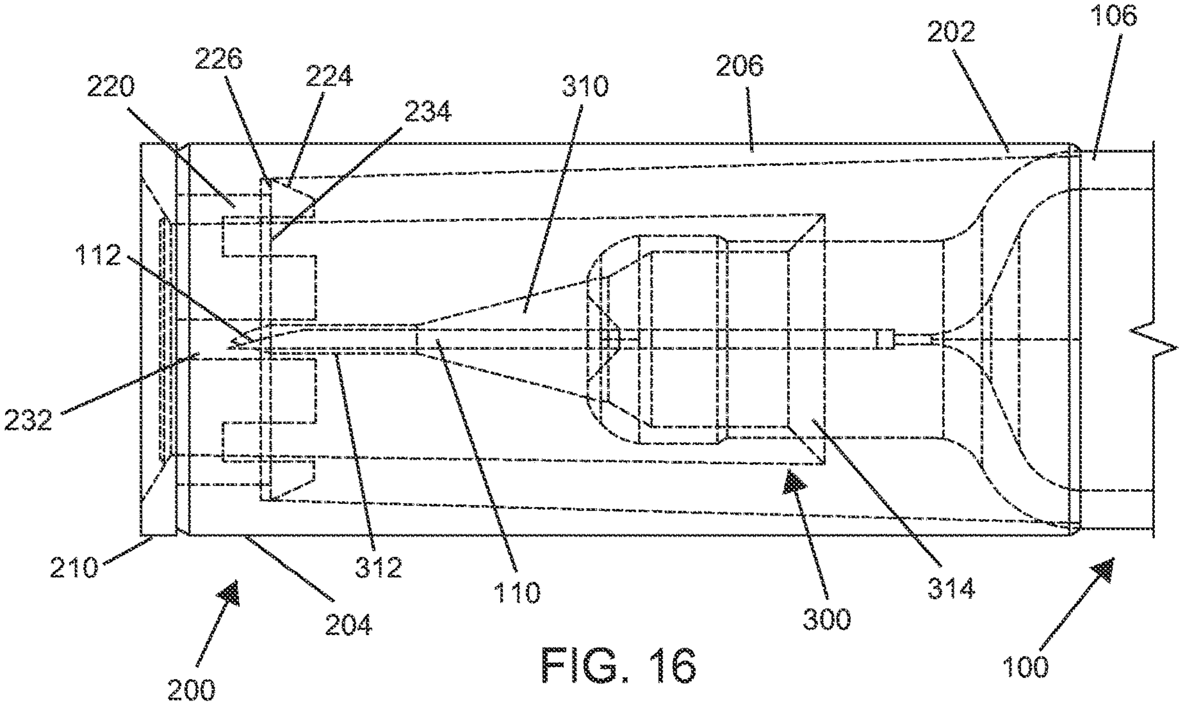
FIG. 16 is a side detail view of the RNS fully installed on the syringe of FIG. 1.

Referring now to FIGS. 8-10, assembly of the elastomeric insert 300 to the RNS 200 is illustrated. The elastomeric insert 300 is inserted in the RNS 200 prior to attaching the RNS 200 to the syringe 100. The elastomeric insert 300 is inserted in the RNS 200 from the proximal end 202 of the RNS 200, and is advanced through the bore 232 until the distal lip 304 of the elastomeric insert 300 extends through the end cap 210 and engages the lip surface 212. As noted above, the tapered or frusto-conical shape of the body 302 limits the depth that the elastomeric insert 300 can be inserted into the bore 232. In the assembled position, shown in FIG. 10, an outer surface of the body 302 of the elastomeric insert 300 engages, or comes in close proximity to, inner surfaces of the frangible tabs 220. As can be appreciated from FIGS. 8-10, assembly of the elastomeric insert 300 to the RNS 200 is achieved along a single axis, and the various features of these components, namely the bore 232, the lip surface 212, and the body 302, assist in orienting and guiding the elastomeric insert 300 and the RNS 200 during assembly. As such, assembly is simple and reliable. Referring now to FIGS. 11-16, attachment of the RNS 200, including the elastomeric insert 300, to the syringe 100 is illustrated. As shown in FIGS. 11-13, the RNS 200 is slid in a proximal direction onto the syringe 100 until the proximal end 202 of the RNS 200 engages the barrel 106 of syringe 100. At this stage, the tip 112 of the needle 110 is located within the internal cavity 310 of the elastomeric insert 300. Depending on the length of the needle bore 312, the tip 112 of the needle 110 can be located within the needle bore 312, though the tip 112 should not be located at a distalmost end of the needle bore 312 because further proximal movement of the elastomeric insert 300 will subsequently occur. In the position shown in FIG. 13, the proximal end 202 of the RNS 200 engages the barrel 106 of the syringe 100 such that further proximal movement of the RNS 200 relative to the syringe 100 is prevented. As shown in FIG. 14, continued application of force to end cap 210 of the RNS 200 causes the frangible tabs 220 to break from the sidewall 230 and begin sliding through the bore 232 as the ramped surfaces 224 allow the frangible tabs 220 to deflect radially inward. As the end cap 210 moves proximally relative to the main body 206 of the RNS 200, the elastomeric insert 300 moves along with the end cap 210 due to engagement of the distal lip 304 with the lip surface 212 (as shown in FIG. 10). Additionally, the radially inward deflection of the frangible tabs 220 causes the frangible tabs 220 to compress against the elastomeric insert 300, further locking the elastomeric insert 300 to the end cap 210. As the elastomeric insert 300 continues to slide proximally with the end cap 210, the tip 112 of the needle 110 is advanced distally within the needle bore 312 of the elastomeric insert 300. Compression of the frangible tabs 220 against the elastomeric insert 300 squeezes the needle bore 312 against the needle 110, reducing the diameter of the needle bore 312 to seal the needle tip 112. The end cap 210 can be moved proximally until the end cap 210 contacts the main body 206, as shown in FIGS. 15 and 16. At this stage, the locking surfaces 226 of the frangible tabs 220 have cleared the shoulder 234 of the main body 206, allowing the frangible tabs 220 to deflect radially outward. Upon outward deflection of the frangible tabs 220, the locking surfaces 226 engage the shoulder 234. The outward deflection of the frangible tabs 220 is limited by the diameter at the outer edge of the shoulder 234, which is less than the outer diameter of the frangible tabs 220 prior to being broken from the end cap 210. As such, the frangible tabs 220 are still subject to a radial inward load which compresses the elastomeric insert 300. In this position, the RNS 200 is fully attached to the syringe 100. As noted above, the tip 112 of the needle 110 is located within the needle bore 212, and the frangible tabs 220 compress the elastomeric insert 300 to seal the tip 112. Despite that the frangible tabs 220 relax somewhat as the locking surfaces 226 clear the shoulder 234, the frangible tabs 220 still provide sufficient compression to the elastomeric insert 300 to achieve a sterile seal of the tip 112. In particular, the diameter of the elastomeric insert 300 when sealing the tip 112 may be compressed between approximately 5% and approximately 15% relative to the initial, uncompressed diameter of the elastomeric insert 300.

At no stage in the process of installing the RNS 200 onto the syringe 100 is significant lateral loading introduced to the needle 100. Thus, the RNS 200 is suitable for use with syringes 100 having small-diameter needles (e.g. 25 gauge and smaller), thin-wall needles, and needles otherwise susceptible to breakage from lateral loads. However, the present disclosure is not limited to needles of small diameter, and could be used on larger needles, such 22 gauge or larger provided appropriate geometry is used for the components of the RNS. Furthermore, the tip 112 of the needle 110 is not required to pierce the elastomeric insert 300 in order to enter the needles bore 312 and establish a seal. Rather, as noted above, the seal is created by compression of the elastomeric insert 300 around the needle 100, and more precisely around an outer surface of the needle 100. Therefore, attachment of the RNS 200 to the syringe 100 does not significantly dull the tip 112 of the needle 100.

In the fully attached position of the RNS 200 shown in FIGS. 15 and 16, the end cap 210 is prevented from moving distally relative to the main body 206 due to the engagement of the locking surfaces 226 with the shoulder 234. Thus, once the RNS 200 has been fully attached to the syringe 100, pulling distally on the end cap 210 causes the entirety of the RNS 200, including the end cap 210 and the main body 206, to detach from the syringe 100. Removal of the RNS 200 from the syringe 100 can therefore be accomplished by pulling distally on any portion of the RNS 200. The elastomeric insert 300 remains attached to the end cap 210 during removal of the RNS 200 due to engagement of the distal lip 304 of the elastomeric insert 300 engaging the lip surface 212 of the end cap 210. Once removed from the syringe 100, the RNS 200 is hygienically disposed of and cannot be reused.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A rigid needle shield for a syringe, the rigid needle shield comprising:

a main body comprising an internal sidewall defining a bore, an end cap attached to the main body, the end cap comprising at least one frangible tab with an integral connection formed with the sidewall of the main body at a tip of the at least one frangible tab;

an elastomeric insert extending through the bore and engaging the end cap, wherein the elastomeric insert defines an internal cavity having a needle bore for receiving a needle of the syringe, wherein the at least one frangible tab is configured to break the integral connection from the internal sidewall and advance through the bore between the internal sidewall and the elastomeric insert upon application of a force to the end cap;

wherein each of the at least one frangible tabs comprises an at least partially protruding surface configured to cause the frangible tab to deflect radially inward to allow the frangible tab to advance through the bore; and wherein deflection of the at least one frangible tab causes radial compression of the elastomeric insert and reduces the diameter of the needle bore.

2. The rigid needle shield of claim 1, wherein each of the at least one frangible tabs comprises a locking surface configure to engage a shoulder of the main body.

3. The rigid needle shield of claim 2, wherein engagement of the locking surface and the shoulder prohibits proximal movement of the end cap relative to the main body.

4. The rigid needle shield of claim 1, wherein the needle bore is sized for a clearance fit with the needle of the syringe.

5. The rigid needle shield of claim 1, wherein the elastomeric insert comprises a distal lip configured to engage a lip surface of the end cap.

6. The rigid needle shield of claim 1, wherein the at least one frangible tab is arranged in a ring about the bore.

7. The rigid needle shield of claim 1, wherein the end cap defines a gap between adjacent frangible tabs.

8. The rigid needle shield of claim 1, wherein the rigid needle shield comprises two, three, or four frangible tabs.

9. The rigid needle shield of claim 1, wherein a body of the elastomeric insert is tapered.

10. A system comprising:

a syringe comprising a barrel and a needle;

a rigid needle shield attached to a distal end of the syringe, the rigid needle shield comprising:

a main body comprising an internal sidewall defining a bore;

an end cap attached to the main body, the end cap comprising at least one frangible tab with an integral connection formed with the sidewall of the main body at a tip of the at least one frangible tab;

an elastomeric insert extending through the bore and engaging the end cap, wherein the elastomeric insert defines an internal cavity having a needle bore for receiving a needle of the syringe, wherein the at least one frangible tab is configured to break the integral connection from the internal sidewall and advance through the bore between the internal sidewall and the elastomeric insert upon application of a force to the end cap;

wherein each of the at least one frangible tabs comprises an at least partially protruding surface configured to cause the frangible tab to deflect radially inward to allow the frangible tab to advance through the bore; and wherein deflection of the at least one frangible tab causes radial compression of the elastomeric insert and reduces the diameter of the needle bore.

11. The system of claim 10, wherein a proximal end of the rigid needle shield engages the barrel of the syringe.

12. The system of claim 10, wherein the at least one frangible tab is configured to break after the proximal end of the rigid needle shield has engaged the barrel of the syringe.

13. The system of claim 10, wherein the elastomeric insert defines a needle bore having a clearance fit with the needle.

14. The system of claim 10, wherein deflection of the at least one frangible tab causes compression of the elastomeric insert and squeezes the needle to seal a tip of the needle.

15. The system of claim 10, wherein a tip of the needle does not pierce the elastomeric insert in order to enter the needle bore.

16. The system of claim 10, wherein the elastomeric insert defines a proximal bore configured to engage a tip of the barrel of the syringe.

17. The system of claim 10, wherein the needle is 25 gauge or smaller.

* * * * *